United States Patent [19]
Horsler

[11] Patent Number: 6,153,214
[45] Date of Patent: Nov. 28, 2000

[54] WOUND DRESSING AND MANUFACTURE THEREOF

[75] Inventor: Jo Ann Horsler, Coventry, United Kingdom

[73] Assignee: Tencel Limited, Derby, United Kingdom

[21] Appl. No.: 09/254,213

[22] PCT Filed: Sep. 5, 1997

[86] PCT No.: PCT/GB97/02385

§ 371 Date: Mar. 3, 1999

§ 102(e) Date: Mar. 3, 1999

[87] PCT Pub. No.: WO98/09663

PCT Pub. Date: Mar. 12, 1998

[30] Foreign Application Priority Data

Sep. 5, 1996 [GB] United Kingdom ............ 9618573

[51] Int. Cl.⁷ .................. A61K 9/70; A61F 13/00
[52] U.S. Cl. ........................................... 424/443
[58] Field of Search ............................... 424/445

[56] References Cited

U.S. PATENT DOCUMENTS 4,579,943  4/1986  Kamide et al. ..................... 536/98
5,470,576  11/1995  Patel ................................ 424/445

FOREIGN PATENT DOCUMENTS

| 344913 | 12/1989 | European Pat. Off. . |
| 586260 | 3/1994 | European Pat. Off. . |
| 2276819 | 10/1994 | United Kingdom . |
| WO93/12275 | 6/1993 | WIPO . |
| WO94/16746 | 8/1994 | WIPO . |
| WO95/19795 | 7/1995 | WIPO . |
| WO98/09663 | 3/1998 | WIPO . |

OTHER PUBLICATIONS

S. Thomas et al, "Examining the Properties and Uses of Two Hydrogel Sheet Dressings", *Journal of Wound Care*, 2(3):176–179 (May, 1993).

*Primary Examiner*—S. Mark Clardy
*Assistant Examiner*—Konata M. George
*Attorney, Agent, or Firm*—Howson and Howson

[57] ABSTRACT

Gel sheets suitable for use as wound dressings can be made by thoroughly wetting with an aqueous liquor a textile material which comprises at least 50 percent by weight of a water-swellable fiber and subsequently pressing the thusly-formed swollen sheet.

10 Claims, No Drawings

WOUND DRESSING AND MANUFACTURE THEREOF

FIELD OF THE INVENTION

This invention relates to improvements in hydrogel sheet dressings, that is to say dressings in the form of a gel sheet, namely a sheet comprising a major proportion of water and a minor proportion of polymeric material, and in methods of manufacturing the same.

BACKGROUND ART

Various types of hydrogel sheet dressing are known and are available commercially. The properties of two such dressings are reported by S Thomas in J. Wound Care, 1993, 2, 176. Hydrogels have been recommended for use as wound contact layers. Desirably, a wound contact layer should be non-adherent, conformable and permeable to aqueous liquids such as wound exudate and should maintain its integrity during use.

DISCLOSURE OF THE INVENTION

According to the invention there is provided a method of manufacturing a wound dressing in the form of a gel sheet, characterised in that a textile material comprising at least 50 percent by weight of a gel-forming fibre is thoroughly wetted with an aqueous liquor and then pressed, thereby forming the gel sheet.

The textile material may consist essentially of the gel-forming fibre, or it may contain in its body or as backing layer reinforcement in the form of fibre or scrim which is not gel-forming. The presence of such reinforcement assists in maintaining dimensional stability through the pressing step. Textile materials which comprise at least 75 or at least 90 percent by weight of the gel-forming fibre may be preferred.

The textile material may be a bonded carded fibre web or a knitted or woven fabric, but it is preferably a nonwoven fabric such as a spunlaced or needled fabric. The basis weight of the textile material is preferably in the range from 20 to 1000, more preferably 50 to 250, g/m². The textile material may additionally comprise solid material in powder form, for example a hydrophilic or superabsorbent polymer.

Suitable gel-forming fibres include alginate-based fibres, in particular calcium alginate fibres, carboxymethylated cellulose (CMC) fibres such as those disclosed in U.S. Pat. No. 4,579,943 and WO-A-93/12275, in particular carboxymethylated lyocell fibres, and fibres of cross-linked polymers based on acrylic acid such as those disclosed in EP-A-0,269,393, EP-A-0,397,410 and WO-A-94/04724. For calcium alginate fibres, fibres of the high-M type (e.g. containing from 50 to 75 percent by weight mannuronic acid) may be preferred. Other examples of gel-forming fibres include fibres based on pectin, chitosan, hyaluronic acid and other polysaccharides derived from gums. Blends of gel-forming fibres may be used.

The aqueous liquor may be water but is preferably a saline solution, for example containing from 0.1 to 5.0, often about 0.9, percent by weight sodium chloride, preferably physiological saline. If desired, the aqueous liquor may contain ions which exhibit physiological activity, for example silver or zinc cations. A wound dressing produced by the method of the invention may have hypotonic or hypertonic properties, depending on its salt content. The aqueous liquor may be an aqueous alcohol, for example aqueous ethanol, to permit greater control in the wetting and pressing steps. The aqueous liquor may additionally comprise one or more dissolved or dispersed substances which it is desired to incorporate into the dressing. Examples of such substances include conventional substances used as preservatives, humectants such as propylene glycol, antimicrobial agents, pharmaceutical agents, analgesics, non-stick compositions such as silicore emulsions, wound-healing agents, odour-absorbing agents and fragrances. An aqueous liquor which comprises from 5 to 25 percent by weight propylene glycol may confer the benefits both of process control and of the incorporation of this substance in the dressing.

The textile material may conveniently be wetted with the aqueous liquor by immersion therein. In the case of alginate fibres, a weight ratio of liquor to textile material in the range from 100:1 to 500:1 may be found convenient. In the case of CMC fibres, a weight ratio in the range from 10:1 to 100:1, preferably from 25:1 to 50:1, may be found convenient. Nevertheless, this ratio is in general not critical, provided that it is sufficiently high so that the textile material is gelatinised by the thorough wetting. This gelatinised material is swollen in comparison with the textile material, and it generally takes the form of a transparent or translucent sheet having mechanical integrity.

The degree of pressure to be applied in the pressing step depends both on the nature of the starting materials and on the desired characteristics, in particular the absorbency, of the wound dressing to be produced. In general, pressures in the range from 500 to 7500 kPa (gauge) may be found to give good results in batchwise processes. If desired, the dressing may be embossed or perforated during the pressing step.

The method of the invention may be carried out continuously or batchwise. Continuous operation may be achieved by pressing by means of calender rolls. It is preferred to restrict the widthwise expansion of the gel sheet during calendering, for example by enclosing the sheet in a flattened fabric tube or by constraining it between side walls.

The thickness of a gel sheet produced by the method of the invention is often in the range from 0.5 to 2.5 mm. The basis weight of a gel sheet produced by the method of the invention is often in the range from 50 to 5000, preferably from 100 to 1500, g/m². The total solids content of a gel sheet produced by the method of the invention (including polymer solids derived from the gel-forming fibre and any salts derived from the aqueous liquor) is often in the range from 5 to 40 percent by weight.

Gel sheets produced by the method of the invention may be sterilised, for example by autoclaving or gamma or electron-beam irradiation. In contrast, irradiation may often be found to have adverse effects on the properties of some known types of gel sheet dressings.

If desired, the gel sheet produced by the method of the invention may be furnished with a backing layer, for example in the form of an absorbent wadding, a net or mesh, or a film. If such a backing is applied to the gel sheet before or during pressing by calendering, it may serve to restrict widthwise expansion.

Gel sheets produced by the method of the invention are easier to handle than known hydrogel sheet dressings, on account of their superior tensile properties and low tendency to self-adherence. They are less susceptible to drying out and consequent embrittlement when left exposed than other gel sheets are. Gel sheets produced by the method of the invention have good non-adherent properties with respect to wound surfaces, and they may become more non-adherent after they have absorbed a small quantity of exudate. Gel sheets produced by the method of the invention stay intact even when saturated with exudate. They exhibit an adequate absorption capacity, a rapid absorption rate and an excellent ability to transmit exudate to a secondary backing dressing. They have a rubbery handle and are highly conformable to wound surfaces.

Gel sheets produced by the method of the invention are useful as wound contact layers alone or in composite dressings. They have a particular advantage of low adherency to wounds in comparison to known wound-contacting materials such as knitted fabrics. They are capable of creating and maintaining a desirable moist environment, beneficial to wound healing. Gel sheets produced by the method of the invention also find application as absorbent layers in composite wound dressings, where they show advantageous combinations of absorption capacity and vapour permeability properties.

The invention is illustrated by the following Examples, in which parts and proportions are by weight unless otherwise specified.

EXAMPLE 1

Needled nonwoven staple fibre fabric (ca. 100 g/m$^2$) was immersed in 0.9% saline solution for a few seconds to allow liquor absorption to occur and then pressed for 1 minute using a hydraulic press between 100 micron mesh sheets backed with woodpulp sheets as blotters to yield a gel sheet. For calcium alginate fabric, a liquor/fibre ratio of at least 400:1 was used in order to obtain the desired degree of gelation of the fibres. For carboxymethylated cellulose fabric, a liquor/fibre ratio of 30:1 was generally used.

Samples of the gel sheet were sterilised by placing in Schott bottles and autoclaving at 121° C. for 25 minutes.

Sample thickness was measured using a Shirley Thickness Gauge (AS18) with a weight applying a pressure of 30 g/cm$^2$. Weight per unit area was measured on samples 5 cm square. Solids content was measured on samples 5 cm square by drying in an oven at 105° C. for 4 hours. Tensile tests were performed on samples 45 mm long×25 mm wide, using an Instron (Trade Mark) tensile testing machine with head speed 100 mm/min. Absorbency was measured by the method described in British Pharmacopoeia 1993, Addendum 1995, page 1706 under the title "Alginate Dressings—Absorbency". Fluid handling properties were measured by the method described in British Pharmacopoeia 1993, Addendum 1995, pages 1943–1944 under the title "Semipermeable Hydrocolloid Dressing—Fluid Handling", except that measurements were made at 25° C.; this test is designed to measure the total fluid-handling capacity of a dressing, both by absorption and by water vapour transmission.

Liquid permeability properties of dressings were measured as follows. The sample to be tested (50 mm square) is placed between horizontally-disposed Perspex (Trade Mark) sheets (110 mm square×3 mm thick). The sample is backed by a piece of viscose needlefelt wadding, 45 mm square of basis weight ca. 300 g/m$^2$. The lower sheet has a central hole joined using 5 mm ID tubing by way of a T-connector to a 1 ml pipette serving as manometric leg and to a peristaltic pump capable of delivering 0.5 ml/min. The pump is supplied from a fluid reservoir containing water (142 mM Na, 2.5 mM Ca). Liquid level is adjusted to the upper surface of the lower plate, and the pump is switched on. The behaviour of the sample is observed; liquid leakage from under the sample is adjudged failure, whereas passage of liquid through the sample so as to saturate the backing is adjudged success.

A needled nonwoven fabric (100 g/m$^2$) of carboxymethylated lyocell fibres (1.7 dtex, 50 mm, 0.35 D.S.) (available from Courtaulds Fibres (Holdings) Limited) was treated as described above but at a variety of different pressures during the pressing step to form a gel sheet. A needled nonwoven fabric (100 g/m$^2$) of high-M calcium alginate fibres (3 dtex, 50 mm) was likewise treated as described above to form a gel sheet. A needled nonwoven fabric of high-G calcium alginate fibres was also tested, but failed to gel satisfactorily under the conditions of the experiment, so that no gel sheet was formed. The results shown in Table 1 were obtained with the carboxymethylated lyocell:

TABLE 1

| Pressure kPa (psig) | Thickness mm | Basis weight g/m$^2$ | Solids % | M/D Breaking Load N/cm | M/D Extension at break % | X/D Breaking Load N/cm | X/D Extension at break % |
|---|---|---|---|---|---|---|---|
| Carboxymethylated lyocell | | | | | | | |
| 690 (100) | 1.11 | 1393 | 12.2 | 1.25 | 29.3 | 1.64 | 39.5 |
| 1380 (200) | — | — | 13.0 | 2.04 | 41.9 | 3.42 | 28.1 |
| 2070 (300) | — | — | 17.4 | 1.94 | 12.2 | 9.66 | 35.8 |
| 2760 (400) | — | — | 18.0 | 3.54 | 24.0 | 7.34 | 30.1 |
| 3450 (500) | 0.77 | 497 | 22.5 | 2.80 | 19.9 | 10.8 | 50.0 |
| 6900 (1000) | 0.61 | 235 | 30.1 | 6.82 | 28.9 | 20.0 | 32.5 |

M/D stands for machine direction, X/D for cross direction. A dash in this and other Tables indicates that no measurement was made.

The properties (measured as described above) of a number of commercial hydrogel and hydrocolloid sheet dressings used for comparison are shown in Table 2:

TABLE 2

| Sample | Thickness mm | Basis weight g/m$^2$ | Solids % | Nature |
|---|---|---|---|---|
| Vigilon | 0.99 | 1270 | 5.6 | Hydrogel |
| Geliperm | 2.29 | 2870 | 5.1 | Hydrogel |
| Granuflex | 2.50 | 3810 | — | Hydrocolloid |
| Comfeel | 1.30 | 3400 | — | Hydrocolloid |

Vigilon is a Trade Mark of Bard Limited. Geliperm is a Trade Mark of Geistlich Sons Limited. Granuflex is a Trade Mark of ConvaTec Limited. Comfeel is a Trade Mark of Coloplast Limited. The properties of all these materials are described by S. Thomas in Handbook of Wound Dressings, published by Journal of Woundcare, Macmillan Magazines Ltd. (1994).

The absorbencies of gel sheets made by the method of the invention with pressing at various pressures and of commercial gel sheets are compared in Table 3:

TABLE 3

| Sample | g/g/ 30 min | g/100 cm$^2$/ 30 min | g/g/24 hr | g/100 cm$^2$/ 24 hr |
|---|---|---|---|---|
| Carboxymethylated lyocell: | | | | |
| 690 kPa | 0.35 | 5.7 | — | — |
| 3450 kPa | 0.99 | 4.7 | — | — |
| 6900 kPa | 1.05 | 4.5 | 1.09 | 4.63 |
| Alginate (6900 kPa) | 0.75 | 2.15 | 0.92 | 2.83 |
| Vigilon | 0.37 | 5.10 | 0.73 | 9.01 |
| Geliperm | 0.12 | 3.61 | 0.72 | 8.89 |
| Granuflex | 0.11 | 1.63 | 1.04 | 15.4 |
| Comfeel | 0.07 | 1.01 | 1.13 | 15.6 |

The fluid-handling properties of gel sheets made by the method of the invention and of commercial gel sheets are compared in Table 4:

TABLE 4

| Sample | Total Fluid Handling Capacity g/10 cm$^2$/24 hr | Vapour Loss g/10 cm$^2$/24 hr | Fluid Retained (by difference) |
|---|---|---|---|
| Carboxymethylated lyocell: | | | |
| 690 kPa | 1.7 | 2.7 | −1.1 |
| 3450 kPa | 2.1 | 1.7 | 0.5 |
| 6900 kPa | 3.3 | 2.8 | 0.5 |
| Alginate (6900 kPa) | 3.4 | 2.6 | 0.8 |
| Vigilon | 2.2 | 2.5 | −0.3 |
| Geliperm | 1.0 | 4.3 | −3.3 |
| Granuflex | 1.0 | 0.1 | 0.9 |
| Comfeel | 1.0 | 0.1 | 1.0 |

Gel sheets made by the method of the invention had a notably high fluid handling capacity. The more highly-pressed samples absorbed more moisture than they lost by evaporation.

The liquid permeability properties of gel sheets made by the method of the invention and of a commercial material when simulating use as facing layers in wound dressings are compared in Table 5:

TABLE 5

| Carboxymethylated lyocell (6900 kPa) | Pass |
|---|---|
| Calcium alginate (high-M) (6900 kPa) | Fail |
| Tricotex | Pass |
| Geliperm | Fail |

Tricotex (Trade Mark of Smith & Nephew) is an open mesh knitted fabric of continuous filament viscose rayon, designed as a facing layer for dressings used in the treatment of heavily exuding wounds, for example burns and leg ulcers. It is alleged to be non-adherent, so that it can be removed from the patient with minimal discomfort, although its properties in this respect have been reported to be less good than might be desired (S. Thomas, J. Wound Care, 1994, 3 (1), 27).

Conformability of dressings was assessed by measuring bending length according to British Standard 3356:1990 and the load required to induce 5% extension using an Instron tensile testing machine. The results shown in Table 6 were obtained:

TABLE 6

| Sample | Bending length cm | Load N at 5% extension |
|---|---|---|
| Carboxymethylated lyocell (6900 kPa) M/D | 0.72 | 0.05 |
| Carboxymethylated lyocell (6900 kpa) X/D | 0.61 | 0.15 |
| Tricotex (weft direction) | 2.52 | 2.00 |
| Tricotex (warp direction) | 2.55 | 0.60 |
| Granuflex (absorbent side up) | 2.93 | 0.90 |
| Granuflex (absorbent side down) | 2.04 | 0.90 |
| Geliperm | 0.55 | — |

Geliperm was found to be highly elastic and the load required to induce 5% extension was too low to record. The dressings prepared according to the method of the invention exhibited a desirable combination of mechanical integrity, flexibility and conformability. cl EXAMPLE 2

A needled nonwoven fabric 10 cm×10 cm of carboxymethylated lyocell fibres as used in Example 1 (1 part) was immersed in a mixture (30 parts) of 0.9% saline solution (85 parts) and propylene glycol (15 parts) until thoroughly wetted and gelled. The fabric was removed from the liquor and excess liquor was removed either by draining and blotting or by vacuum extraction. Sample weight at this stage is typically 10–15 g. The fabric was inserted into one end of a stockinette of open netting construction slightly wider (when flattened) than the width of the fabric and approximately five times longer than the length of the fabric. The fabric-containing end of the stockinette was sandwiched between sheets of absorbent paper (supplied from undriven reels) disposed either side of the stockinette and fed into the nip between a pair of calender rollers. Speed through the calender was 1 m/min, the gap between the calender rollers was 0.18 mm (0.007 in) and the recorded pressure applied to the rollers was 968 kPa (100 psi). The excess length of the stockinette allows for the lengthwise expansion in this dimension during this pressing step. The paper sheets were removed and discarded, and the gel sheet was removed from the stockinette. The basis weight of the gel sheet was 731 g/m² (average of 10 samples).

In a further experiment in which the gap between the rollers was 0.1 mm (0.004 in), a basis weight of 623 g/m² (average of 5 samples) was obtained.

What is claimed is:

1. A method of manufacturing a wound dressing in the form of a gel sheet, in which method a textile material comprising at least 50 percent by weight of a gel-forming fibre is thoroughly wetted with an aqueous liquor and then pressed, thereby forming the gel sheet.

2. A method according to claim 1, wherein the textile material comprises at least 75 percent by weight of the gel-forming fibre.

3. A method according to claim 2, wherein the textile material consists essentially of gel-forming fibre.

4. A method according to claim 1, wherein the textile material is a nonwoven fabric.

5. A method according to claim 1, wherein the textile material has a basic weight in the range from 20 to 1000 grams per square meter.

6. A method according to claim 1, wherein the aqueous liquor is a saline solution containing from 0.1 to 5.0 percent by weight sodium chloride.

7. A method according to claim 1, wherein the gel sheet has a solids content in the range from 5 to 40 percent by weight.

8. A method according to claim 1, which includes a step of furnishing the gel sheet with a backing layer.

9. A method according to claim 1, wherein the gel-forming fibres are calcium alginate fibres.

10. A method according to claim 1, wherein the gel-forming fibres are carboxymethylated lyocell fibres.

* * * * *